US008871987B2

(12) United States Patent
Knapp

(10) Patent No.: US 8,871,987 B2
(45) Date of Patent: Oct. 28, 2014

(54) PURIFICATION OF CIS-1,1,1,4,4,4-HEXAFLUORO-2-BUTENE VIA EXTRACTIVE DISTILLATION

(75) Inventor: Jeffrey P. Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 104 days.

(21) Appl. No.: 13/315,365

(22) Filed: Dec. 9, 2011

(65) Prior Publication Data

US 2012/0323054 A1    Dec. 20, 2012

Related U.S. Application Data

(60) Provisional application No. 61/421,829, filed on Dec. 10, 2010.

(51) Int. Cl.
*C07C 17/386* (2006.01)
*C07C 17/383* (2006.01)
*C07C 21/18* (2006.01)

(52) U.S. Cl.
CPC ........... *C07C 17/386* (2013.01); *C07B 2200/09* (2013.01); *C07C 21/18* (2013.01)
USPC ............................. 570/178; 570/180; 570/263

(58) Field of Classification Search
None
See application file for complete search history.

(56) References Cited

U.S. PATENT DOCUMENTS

| | | | | |
|---|---|---|---|---|
| 5,087,329 | A | * | 2/1992 | Felix ................................ 203/67 |
| 5,874,657 | A | * | 2/1999 | Miller et al. ................... 570/178 |
| 7,371,309 | B2 | * | 5/2008 | Boehmer et al. ................. 203/57 |
| 2008/0269532 | A1 | | 10/2008 | Swearingen |
| 2010/0160696 | A1 | * | 6/2010 | Nappa et al. ................... 570/160 |

FOREIGN PATENT DOCUMENTS

| | | |
|---|---|---|
| JP | 302541 | 10/1993 |
| WO | WO 2008030615 A2 * | 3/2008 |
| WO | 2010014548 A2 | 2/2010 |

OTHER PUBLICATIONS

Knapp, J. P. et al. 2004 Distillation, azeotropic, and extractive, Kirk-Othmer Encyclopedia of Chemical Technology (5th Edition), vol. 8, pp. 786-852, Conference; General Review, 2004, CODEN: 69JEDT.*
E.g., W. Schotte Ind. Eng. Chem. Process Des. Dev. (1980) 19, 432-439).
International Search Report, PCT/US2011/064217, International Filing Date Dec. 9, 2011.

* cited by examiner

*Primary Examiner* — Jafar Parsa
*Assistant Examiner* — Medhanit Bahta

(57) ABSTRACT

A process for separating cis-1,1,1,4,4,4-hexafluoro-2-butene from a first mixture comprising cis-1,1,1,4,4,4-hexafluoro-2-butene and at least one chlorofluoroolefin is disclosed. The process involves the steps of contacting the mixture with at least one extractive agent, to form another mixture, distilling the mixture; and recovering cis-1,1,1,4,4,4-hexafluoro-2-butene substantially free of chlorofluoroolefin.

22 Claims, 2 Drawing Sheets

PURIFICATION OF CIS-1,1,1,4,4,4-HEXAFLUORO-2-BUTENE VIA EXTRACTIVE DISTILLATION

CROSS REFERENCE TO RELATED APPLICATIONS

This application claims priority to U.S. Provisional application 61/421,829, filed Dec. 10, 2010.

BACKGROUND INFORMATION

1. Field of the Disclosure

This disclosure relates in general to an extractive distillation process for purifying cis-1,1,1,4,4,4-hexafluoro-2-butene.

2. Description of the Related Art

The fluorocarbon industry has been working for the past few decades to find replacement refrigerants and blowing agents for the ozone depleting chlorofluorocarbons (CFC's) and hydrochlorofluorocarbons (HCFC's) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine and also have a low global warming potential. The production of hydrofluoroolefins (i.e., unsaturated compounds containing only carbon, hydrogen and fluorine), has been the subject of recent interest to provide environmentally desirable products for use as effective replacements for the existing halogenated compounds.

Purification is an important step in manufacturing these compounds. Conventional distillation is typically used to separate desired products from impurities; however, conventional distillation becomes ineffective when the desired compound forms an azeotrope with or has a boiling point close to that of one or more of the impurities. For example, manufacturing 1,1,1,4,4,4-hexafluoro-2-butene (HFO-1336mzz) from $CF_3CCl=CClCF_3$ (CFC-1316mxx) can result in the formation of contaminants, such as 1,1,1,4,4,4-hexafluoro-2-chloro-2-butene (HCFC-1326mxz) and 1,1,1,2,4,4,4-heptafluoro-3-chloro-2-butene (CFC-1317mx). Cis-HFO-1336mzz and trans-HCFC-1326mxz form an azeotrope, making their complete separation by conventional distillation impossible. Cis-HFO-1336mzz forms azeotrope-like compositions with cis-HCFC-1326mxz as well, complicating removal of cis-1326mxz from cis-HFO-1336mzz as well. Cis-HFO-1336mzz also forms an azeotrope with CFC-1317mx, making their complete separation by conventional distillation impossible.

Thus, there is a need to develop other purification processes for the production of hydrofluoroolefins.

SUMMARY

Disclosed is a process for separating cis-1,1,1,4,4,4-hexafluoro-2-butene from a first mixture comprising cis-1,1,1,4,4,4-hexafluoro-2-butene and at least one chlorofluoroolefin, comprising the steps of: contacting said first mixture with at least one extractive agent, to form a second mixture; distilling said second mixture; and recovering cis-1,1,1,4,4,4-hexafluoro-2-butene substantially free of chlorofluoroolefin.

Also disclosed is a process for reducing the concentration of an impurity, comprising distilling a first mixture comprising cis-1,1,1,4,4,4-hexafluoro-2-butene and an impurity of at least one chlorofluoroolefin in the presence of an extractive agent which is a C6 to C14 linear or branched alkane, C6 to C10 cyclic alkane with or without branching, C6 to C12 linear or branched alkene, C6 to C10 cycloalkene, C6 to C10 diene, C1 to C4 chloroalkane, C2 to C4 chloroalkene, or mixtures thereof; recovering cis-1,1,1,4,4,4-hexafluoro-2-butene substantially free of chlorofluoroolefin as an overhead stream from said distillation column.

Also disclosed is a process for reducing the concentration of an impurity, comprising, distilling a first mixture comprising cis-1,1,1,4,4,4-hexafluoro-2-butene and an impurity of at least one chlorofluoroolefin in the presence of an extractive agent which is an alcohol, diol, ketone, lactone, ester, anhydride, aldehyde, ether, nitrile, amide, sulfoxide, pyrrolidone, carbonate, phosphate, diethyl sulfite, dimethyl sulfate, diethyl sulfate, or mixtures thereof, removing a second mixture comprising cis-1,1,1,4,4,4-hexafluoro-2-butene and said extractive agent substantially free of chlorofluoroolefin as a bottoms composition from said distillation column, distilling said second mixture in a second distillation column, and recovering an overhead composition comprising cis-1,1,1,4,4,4-hexafluoro-2-butene substantially free of said extractive agent from the top of said second distillation column.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
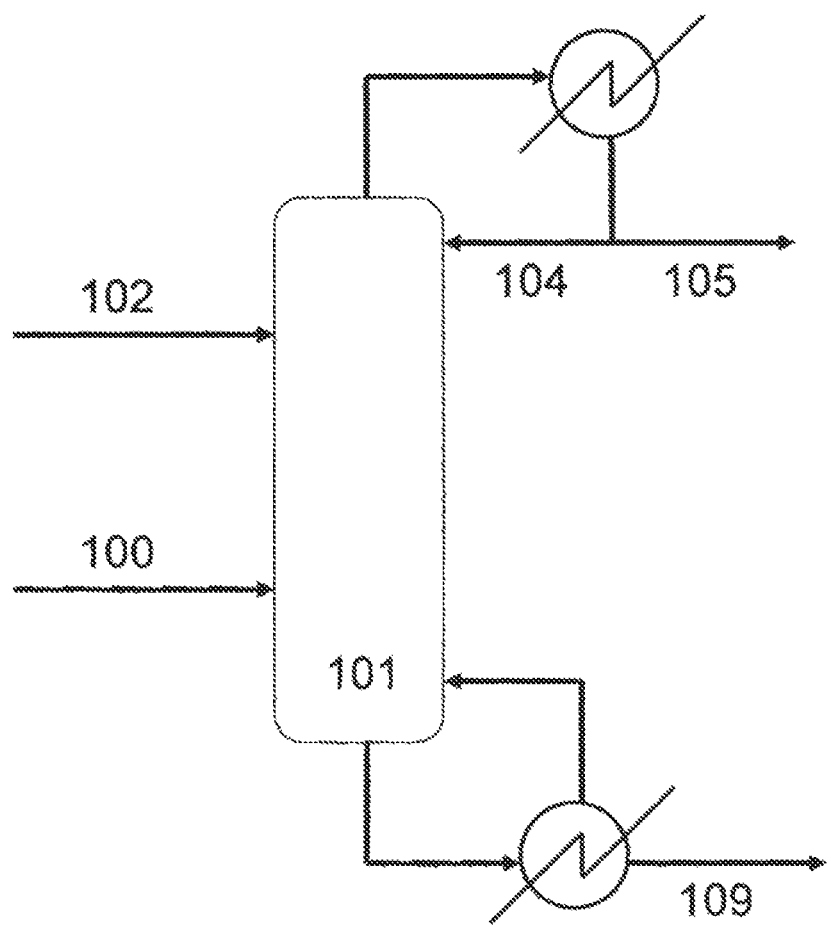
FIG. 1 is a schematic diagram of an extractive distillation system that can be used for practicing an aspect of the present process.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Disclosed is a process for separating cis-1,1,1,4,4,4-hexafluoro-2-butene from a first mixture comprising cis-1,1,1,4,4,4-hexafluoro-2-butene and at least one chlorofluoroolefin, comprising the steps of: contacting said first mixture with at least one extractive agent, to form a second mixture; distilling said second mixture; and recovering cis-1,1,1,4,4,4-hexafluoro-2-butene substantially free of chlorofluoroolefin.

Also disclosed is a process for reducing the concentration of an impurity, comprising distilling a first mixture comprising cis-1,1,1,4,4,4-hexafluoro-2-butene and an impurity of at least one chlorofluoroolefin in the presence of an extractive agent which is a C6 to C14 linear or branched alkane, C6 to C10 cyclic alkane with or without branching, C6 to C12 linear or branched alkene, C6 to C10 cycloalkene, C6 to C10 diene, C1 to C4 chloroalkane, C2 to C4 chloroalkene, or mixtures thereof; recovering cis-1,1,1,4,4,4-hexafluoro-2-butene substantially free of chlorofluoroolefin as an overhead stream from said distillation column.

Also disclosed is a process for reducing the concentration of an impurity, comprising, distilling a first mixture comprising cis-1,1,1,4,4,4-hexafluoro-2-butene and an impurity of at least one chlorofluoroolefin in the presence of an extractive agent which is an alcohol, diol, ketone, lactone, ester, anhydride, aldehyde, ether, nitrile, amide, sulfoxide, pyrrolidone, carbonate, phosphate, diethyl sulfite, dimethyl sulfate, diethyl sulfate, or mixtures thereof; removing a second mixture comprising cis-1,1,1,4,4,4-hexafluoro-2-butene and said extractive agent substantially free of chlorofluoroolefin as a bottoms composition from said distillation column, distilling said second mixture in a second distillation column, and recovering an overhead composition comprising cis-1,1,1,4, 4,4-hexafluoro-2-butene substantially free of said extractive agent from the top of said second distillation column.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

By substantially free or substantially pure, it is meant that the cis-HFO-1336mzz product contains less than about 1000 parts per million by weight (ppm) of chlorofluoroolefin, and preferably less than about 100 ppm of chlorofluoroolefin, and more preferably less than about 10 ppm of chlorofluoroolefin, and even more preferably less than about 1 ppm of chlorofluoroolefin. By impurity is meant any fluorinated compounds other than the cis-HFO-1336mzz that may be present in the cis-HFO-1336mzz product. As referred to herein, unless specifically identified as either trans-HCFC-1326mxz, or cis-HCFC-1326mxz, throughout this specification HCFC-1326 shall refer to either or both of the cis or trans isomers of HCFC-1326. As referred to herein, unless specifically identified as either trans-CFC-1317mx or cis-CFC-1317mx, throughout this specification CFC-1317mx shall refer to either or both of the cis or trans isomers of CFC-1317mx.

In one embodiment, chlorofluoroolefin refers to at least one of trans-HCFC-1326mxz, cis-HCFC-1326mxz, or 1,1,1,2,4, 4,4-heptafluoro-3-chloro-2-butene (CFC-1317mx). In another embodiment, chlorofluoroolefin refers to at least one of trans-HCFC-1326mxz and cis-HCFC-1326mxz.

As used herein, an azeotropic composition is a constant boiling liquid admixture of two or more substances wherein the admixture distills without substantial composition change and behaves as a constant boiling composition. Constant boiling compositions, which are characterized as azeotropic, exhibit either a maximum or a minimum boiling point, as compared with that of the non-azeotropic mixtures of the same substances. Azeotropic compositions as used herein include homogeneous azeotropes which are liquid admixtures of two or more substances that behave as a single substance, in that the vapor, produced by partial evaporation or distillation of the liquid, has the same composition as the liquid. Azeotropic compositions as used herein also include heterogeneous azeotropes where the liquid phase splits into two or more liquid phases. In these embodiments, at the azeotropic point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

For the purpose of this discussion, azeotrope-like composition means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotropic compositions in which during boiling or evaporation, the liquid composition changes to a substantial degree.

Near-azeotropic compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be azeotrope-like.

It is also recognized that both the boiling point and the weight percentages of each component of the azeotropic or azeotrope-like liquid composition may change when the azeotropic or azeotrope-like liquid composition is subjected to boiling at different pressures. Thus, an azeotropic or an azeotrope-like composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432-439). Experimental identification of azeotropic compositions involving the same components may be used to confirm the accuracy of such calculations and/or to modify the calculations at the same or other temperatures and pressures.

Figure 2:
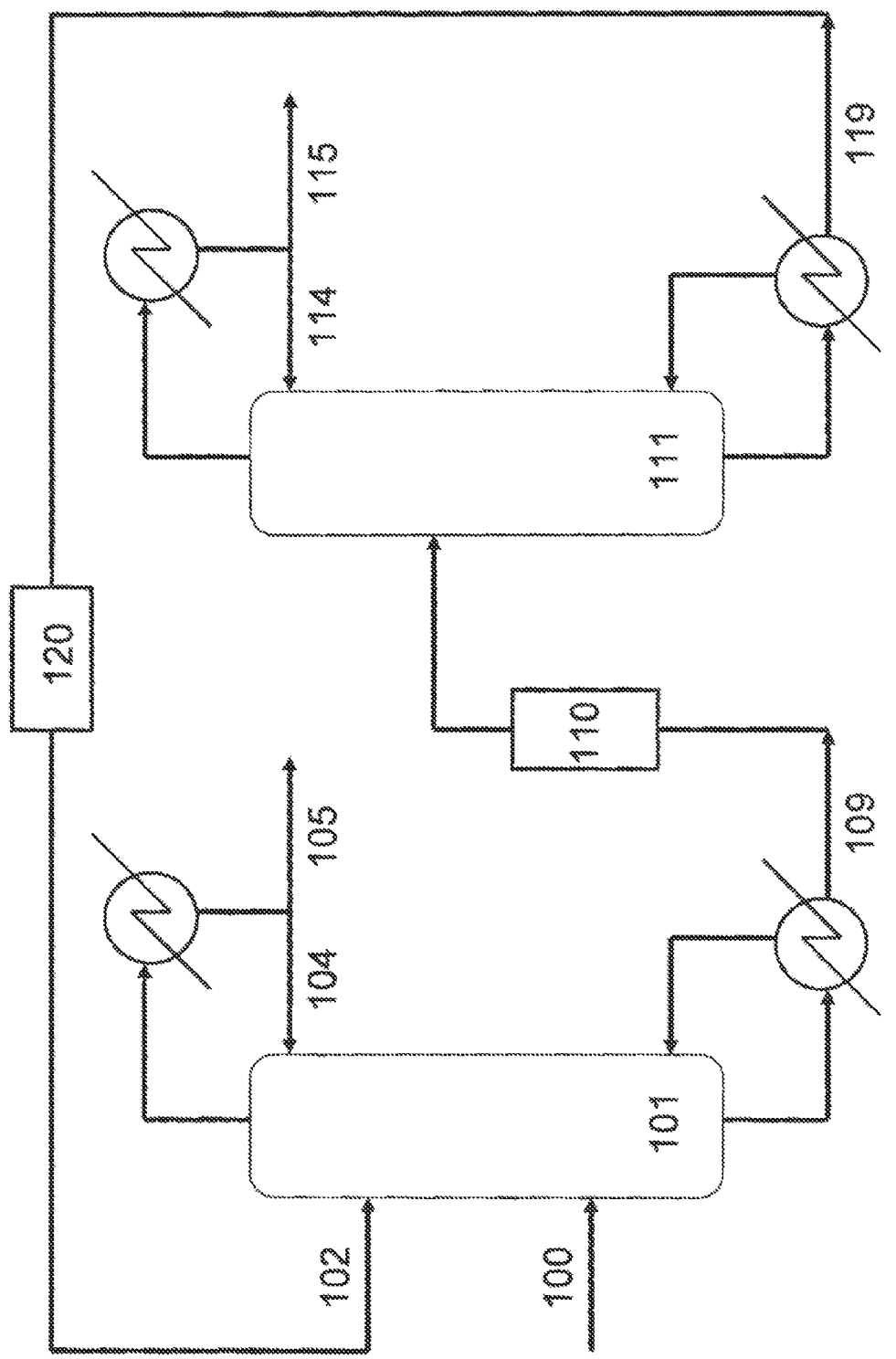
FIG. 2 is a schematic diagram of an extractive distillation system using two columns that can be used for practicing an aspect of the present process.

The present inventive process can be better understood by reference to FIGS. 1 and 2. FIG. 1 schematically illustrates a system which can be used for performing the embodiments of the present extractive distillation process wherein cis-HFO-1336mzz is separated from a first mixture comprising cis-HFO-1336mzz and at least one chlorofluoroolefin using at least one extractive agent. FIG. 2 schematically illustrates a system which can be used for performing the embodiments of the present extractive distillation process wherein cis-HFO-1336mzz is separated from a first mixture comprising cis-HFO-1336mzz and at least one chlorofluoroolefin using at least one extractive agent and wherein the said at least one extractive agent is then recovered and recycled. The systems illustrated by these figures are applicable to both embodiments of the present extractive distillation process wherein the at least one extractive agent increases the relative volatility of cis-HFO-1336mzz compared to at least one chlorofluoroolefin and embodiments wherein the relative volatility of cis-HFO-1336mzz compared to at least one chlorofluoroolefin is decreased using at least one extractive agent.

In one embodiment, a first mixture comprising cis-HFO-1336mzz and at least one chlorofluoroolefin is supplied via conduit 100 to distillation column 101 (see FIG. 1). At least one extractive agent is supplied via conduit 102 to the distillation column 101 at a feed point higher in the column that the feed point of the first mixture. A stream comprising the extractive agent and at least one chlorofluoroolefin is removed from the bottom of column 101 as stream 109. The overhead distillate stream, 105, from column 101 contains concentrated cis-HFO-1336mzz substantially free of chlorofluoroolefin.

In another embodiment, a first mixture comprising cis-HFO-1336mzz and at least one chlorofluoroolefin is supplied via conduit 100 to distillation column 101 (see FIG. 2). At least one extractive agent is supplied via conduit 102 to the distillation column 101 at a feed point higher in the column that the feed point of the first mixture. The overhead distillate stream, 105, from column 101 contains concentrated cis-HFO-1336mzz substantially free of chlorofluoroolefin. A stream comprising the extractive agent and at least one chlorofluoroolefin is removed from the bottom of column 101 as stream 109. In some embodiments, stream 109 is transported to optional heat exchanger 110 and then to stripping column 111 which separates the extractive agent from the at least one chlorofluoroolefin. Extractive agent is removed from the bottom of column 111 via conduit 119 and transported to optional cooler 120 and from there returned to extraction column 101 as the extractive agent feed.

In another embodiment, a first mixture comprising cis-HFO-1336mzz and at least one chlorofluoroolefin is supplied via conduit 100 to distillation column 101 (see FIG. 1). At least one extractive agent is supplied via conduit 102 to the distillation column 101 at a feed point higher in the column that the feed point of the first mixture. A stream comprising the extractive agent and cis-HFO-1336mzz substantially free of chlorofluoroolefin is removed from the bottom of column 101 as stream 109. The overhead distillate, 105, from column 101 contains concentrated chlorofluoroolefin at a higher concentration than in the original mixture.

In yet another embodiment, a first mixture comprising cis-HFO-1336mzz and at least one chlorofluoroolefin is supplied via conduit 100 to distillation column 101 (see FIG. 2). At least one extractive agent is supplied via conduit 102 to the distillation column 101 at a feed point higher in the column that the feed point of the first mixture. A stream comprising the extractive agent and cis-HFO-1336mzz substantially free of chlorofluoroolefin is removed from the bottom of column 101 as stream 109. The overhead distillate, 105, from column 101 contains concentrated chlorofluoroolefin at a higher concentration than in the original mixture. In some embodiments, stream 109 is transported to optional heat exchanger 110 and then to stripping column 111 which separates the extractive agent from cis-HFO-1336mzz. Extractive agent is removed from the bottom of column 111 via conduit 119 and transported to optional cooler 120 and from there returned to extraction column 101 as the extractive agent feed.

In one embodiment, the extractive agent is at least one of a C6 to C14 linear or branched alkane, C6 to C10 cyclic alkane with or without branching, C6 to C12 linear or branched alkene, C6 to C10 cycloalkene, C6 to C10 diene, C1 to C4 chloroalkane, C2 to C4 chloroalkene, or mixtures thereof. In another embodiment, the extractive agent is n-octane or perchloroethylene or mixtures thereof.

In yet another embodiment, the extractive agent is at least one of an alcohol, diol, ketone, lactone, ester, anhydride, aldehyde, ether, nitrile, amide, sulfoxide, pyrrolidone, carbonate, phosphate, diethyl sulfite, dimethyl sulfate, or diethyl sulfate. In another embodiment, the extractive agent is ethyl acetate, n-butanol, 2-butanone, N,N-dimethylformamide, tetrahydrofuran, or mixtures thereof.

In yet another embodiment, the extractive agent is at least one of the compounds listed in Table 1 below.

TABLE 1

| Compound Name | BP (° C.) |
|---|---|
| n-Hexane | 68.7 |
| n-Heptane | 98.4 |
| n-Octane | 125.7 |
| n-Nonane | 150.8 |
| n-Decane | 174.2 |
| n-Undecane | 195.9 |
| n-Dodecane | 216.3 |
| n-Tridecane | 235.5 |
| 2,2,4-Trimethylpentane | 99.2 |
| 2,2,3-Trimethylpentane | 109.8 |
| 2,3,4-Trimethylpentane | 113.5 |
| 2,3,3-Trimethylpentane | 114.8 |
| 2-Methylpentane | 60.3 |
| 3-Methylpentane | 63.3 |
| 2,2-Dimethylpentane | 79.2 |
| 2,4-Dimethylpentane | 80.5 |
| 2,2,3-Trimethylbutane | 80.9 |
| 3,3-Dimethylpentane | 86.1 |
| 2,3-Dimethylpentane | 89.8 |
| 2-Methylhexane | 90.0 |
| 3-Methylhexane | 91.9 |
| 3-Ethylpentane | 93.5 |
| 2,2,3,3-Tetramethylbutane | 106.3 |
| 2,2-Dimethylhexane | 106.8 |
| 2,5-Dimethylhexane | 109.1 |
| 2,4-Dimethylhexane | 109.4 |
| 3,3-Dimethylhexane | 112.0 |
| 2,3-Dimethylhexane | 115.6 |
| 2-Methyl-3-Ethylpentane | 115.7 |
| 2-Methylheptane | 117.7 |
| 4-Methylheptane | 117.7 |
| 3,4-Dimethylhexane | 117.7 |
| 3-Methyl-3-Ethylpentane | 118.3 |
| 3-Ethylhexane | 118.5 |
| 3-Methylheptane | 118.9 |
| 2,2,4,4-Tetramethylpentane | 122.3 |
| 2,2,5-Trimethylhexane | 124.1 |
| 2,4,4-Trimethylhexane | 130.7 |
| 2,2-Dimethylheptane | 132.7 |
| 2,2,3,4-Tetramethylpentane | 133.0 |
| 2,2-Dimethyl-3-Ethylpentane | 133.8 |
| 2,6-Dimethylheptane | 135.2 |
| 2,4-Dimethyl-3-Ethylpentane | 136.7 |
| 2,2,5,5-Tetramethylhexane | 137.5 |
| 2,2,3,3-Tetramethylpentane | 140.3 |
| 2,3,3,4-Tetramethylpentane | 141.6 |
| 4-Methyloctane | 142.4 |
| 3-Ethylheptane | 143.2 |
| 2-Methyloctane | 143.3 |
| 3-Methyloctane | 144.2 |
| 3,3-Diethylpentane | 146.2 |
| 3,3,5-Trimethylheptane | 155.7 |
| 2,4-Dimethyloctane | 155.9 |
| 2,2-Dimethyloctane | 156.9 |
| 2,5-Dimethyloctane | 158.5 |
| 2,7-Dimethyloctane | 159.9 |
| 2,2,3,3-Tetramethylhexane | 160.3 |
| 2,6-Dimethyloctane | 160.4 |
| 2,3-Dimethyloctane | 164.3 |
| 5-Methylnonane | 165.2 |
| 4-Methylnonane | 165.7 |
| 2-Methylnonane | 167.0 |
| 3-Methylnonane | 167.8 |
| 2-Methyldecane | 189.2 |
| 2-Methylundecane | 210.2 |
| 3-Methylundecane | 210.8 |
| 2-Methyldodecane | 229.4 |
| 3-Ethyldodecane | 241.0 |
| 2,2,4,4,6,8,8-Heptamethylnonane | 246.4 |
| 2-Methyltridecane | 247.9 |
| Methylcyclopentane | 71.8 |
| Cyclohexane | 80.7 |
| 1,1-Dimethylcyclopentane | 87.9 |
| cis-1,3-Dimethylcyclopentane | 90.8 |
| trans-1,3-Dimethylcyclopentane | 91.7 |
| trans-1,2-Dimethylcyclopentane | 91.9 |
| cis-1,2-Dimethylcyclopentane | 99.5 |
| Methylcyclohexane | 100.9 |

TABLE 1-continued

| Compound Name | BP (° C.) |
|---|---|
| Ethylcyclopentane | 103.5 |
| 1,1,3-Trimethylcyclopentane | 104.9 |
| 1,1,2-Trimethylcyclopentane | 113.7 |
| 1-cis-2-trans-4-Trimethylcyclopentane | 116.9 |
| 1-cis-2-trans-3-Trimethylcyclopentane | 118.1 |
| Cycloheptane | 118.8 |
| trans-1,4-Dimethylcyclohexane | 119.4 |
| 1,1-Dimethylcyclohexane | 119.6 |
| cis-1,3-Dimethylcyclohexane | 120.1 |
| 1-Methyl-1-Ethylcyclopentane | 121.5 |
| trans-1,2-Dimethylcyclohexane | 123.4 |
| cis-1,4-Dimethylcyclohexane | 124.3 |
| trans-1,3-Dimethylcyclohexane | 124.5 |
| Isopropylcyclopentane | 126.4 |
| cis-1,2-Dimethylcyclohexane | 129.8 |
| n-Propylcyclopentane | 131.0 |
| Ethylcyclohexane | 131.8 |
| 1-trans-3,5-Trimethylcyclohexane | 140.6 |
| Cyclooctane | 151.1 |
| Isopropylcyclohexane | 154.8 |
| n-Butylcyclopentane | 156.6 |
| n-Propylcyclohexane | 156.7 |
| iso-Butylcyclohexane | 171.3 |
| tert-Butylcyclohexane | 171.5 |
| 1,2,3,4-Tetramethylcyclohexane | 176.1 |
| trans-1,4-Diethylcyclohexane | 176.3 |
| 1,1-Diethylcyclohexane | 176.7 |
| sec-Butylcyclohexane | 179.3 |
| n-Butylcyclohexane | 181.0 |
| 1-Hexene | 63.5 |
| 2-Ethyl-1-Butene | 64.7 |
| cis-3-Hexene | 66.5 |
| trans-3-Hexene | 67.1 |
| 3-Methyl-cis-2-pentene | 67.7 |
| trans-2-Hexene | 67.9 |
| cis-2-Hexene | 68.9 |
| 3-Methyl-trans-2-pentene | 70.4 |
| 2,3-Dimethyl-2-butene | 73.2 |
| 2,3,3-Trimethyl-1-butene | 77.9 |
| 3-Methyl-1-hexene | 83.9 |
| 3-Ethyl-1-pentene | 84.1 |
| 5-Methyl-1-hexene | 85.3 |
| 4-Methyl-1-hexene | 86.7 |
| 2-Ethyl-1-pentene | 94.0 |
| trans-3-Heptene | 95.7 |
| cis-3-Heptene | 95.8 |
| trans-2-Heptene | 98.0 |
| cis-2-Heptene | 98.4 |
| 2,4,4-Trimethyl-1-pentene | 101.4 |
| 2,4,4-Trimethyl-2-pentene | 104.9 |
| 2,3-Dimethyl-1-hexene | 110.5 |
| 3-Ethyl-1-hexene | 110.5 |
| 4-Methyl-1-heptene | 112.8 |
| 6-Methyl-1-heptene | 113.2 |
| 2-Methyl-1-heptene | 119.2 |
| 2-Ethyl-1-hexene | 120.0 |
| 1-Octene | 121.3 |
| trans-4-Octene | 122.3 |
| cis-4-Octene | 122.5 |
| cis-3-Octene | 122.9 |
| trans-3-Octene | 123.3 |
| trans-2-Octene | 125.0 |
| cis-2-Octene | 125.6 |
| 7-Methyl-1-octene | 135.0 |
| 2-Methyl-1-octene | 144.7 |
| trans-2-Nonene | 150.1 |
| cis-2-Nonene | 150.8 |
| 2-Methyl-1-nonene | 168.4 |
| 8-Methyl-1-nonene | 170.5 |
| 1-Decene | 170.6 |
| trans-2-Decene | 172.9 |
| cis-2-Decene | 173.9 |
| trans-2,2,4,6,6-Pentamethyl-3-heptene | 180.5 |
| trans-2-Dodecene | 217.9 |
| cis-2-Dodecene | 217.9 |
| 3-Methylcyclopentene | 64.9 |
| 1-Methylcyclopentene | 75.5 |
| 1-Methyl-4-Vinylcyclohexene | 152.0 |

TABLE 1-continued

| Compound Name | BP (° C.) |
|---|---|
| Propenyl Cyclohexene | 158.5 |
| beta-Phellandrene | 174.0 |
| alpha-Phellandrene | 175.0 |
| Terpinolene | 186.9 |
| 1,4-Hexadiene | 65.0 |
| 1,4-Cyclohexadiene | 87.0 |
| 2,5-Dimethyl-1,5-Hexadiene | 114.3 |
| 2,5-Dimethyl-2,4-Hexadiene | 135.3 |
| 1,3,5,7-Cyclooctatetraene | 142.6 |
| 1,5-Cyclooctadiene | 150.1 |
| 1,9-Decadiene | 165.0 |
| 4-isopropyl-1-Methyl-1,3-cyclohexadiene | 175.0 |
| gamma-Terpinene | 183.0 |
| 1,5,9-Cyclododecatriene | 241.5 |
| 3-Hexyne | 81.2 |
| 1-Nonyne | 150.7 |
| 1-Decyne | 174.0 |
| Benzene | 80.1 |
| p-Xylene | 138.4 |
| m-Xylene | 139.1 |
| Styrene | 145.2 |
| p-Ethyltoluene | 162.0 |
| 1,3,5-Trimethylbenzene | 164.7 |
| 1,2,4-Trimethylbenzene | 169.4 |
| p-Cymene | 177.1 |
| 1-Methyl-3-Propylbenzene | 181.8 |
| 2-Phenylbutene-1 | 182.0 |
| p-Methylpropylbenzene | 183.3 |
| 5-Ethyl-m-Xylene | 183.8 |
| p-Diethylbenzene | 183.8 |
| 1-Methyl-2-Propylbenzene | 184.8 |
| o-Ethylstyrene | 187.3 |
| trans-Decahydronaphthalene | 187.3 |
| 1-Ethyl-2-Isopropylbenzene | 193.0 |
| cis-Decahydronaphthalene | 195.8 |
| 1-Methylindene | 198.5 |
| 1,4-Divinylbenzene | 201.1 |
| n-Pentylbenzene | 205.5 |
| 2-Methylindene | 206.3 |
| 1,2,3,4-Tetrahydronaphthalene | 207.6 |
| 1,2,4-Trimethyl-5-Ethylbenzene | 212.0 |
| p-tert-Butyl Ethylbenzene | 212.1 |
| 1,3,5-Triethylbenzene | 215.9 |
| 1,2,3-Triethylbenzene | 217.6 |
| 1,2,4-Triethylbenzene | 218.0 |
| n-Hexylbenzene | 226.1 |
| p-tert-Butylstyrene | 226.9 |
| 1,3,5-Triisopropylbenzene | 238.0 |
| 1-isopropenyl-4-Vinyl Benzene | 241.9 |
| n-Heptylbenzene | 246.1 |
| 1,2,3,5-Tetraethylbenzene | 248.9 |
| HFC-43-10mee | 54.6 |
| Perfluorohexane | 57.2 |
| trans-CFC-1316mxx | 67.9 |
| Perfluoroheptenes | 70.6 |
| Hexafluorobenzene | 80.3 |
| n-Perfluoroheptane | 82.5 |
| 1,4-Difluorobenzene | 88.9 |
| Perfluorononenes | 113.1 |
| Perfluorooctane | 103.3 |
| Perfluorononane | 125.3 |
| Perfluorodecane | 144.2 |
| Perfluorododecane | 178.0 |
| Perfluorohexadecane | 239.0 |
| Carbon Tetrachloride | 76.6 |
| 2,3-Dichlorobutane | 119.5 |
| Perchloroethylene | 121.3 |
| 1,4-Dichloro-cis-2-Butene | 152.5 |
| 1,4-Dichloro-trans-2-Butene | 156.1 |
| p-Dichlorobenzene | 174.1 |
| 1,3,5-Trichlorobenzene | 208.4 |
| Hexachloro-1,3-Butadiene | 213.0 |
| 1,4-Dioxane | 101.3 |
| Tetramethylethylenediamine | 121.0 |
| Tin Tetrachloride | 113.8 |
| Tetranitromethane | 125.7 |
| Titanium Tetrachloride | 135.9 |
| Vanadium Tetrachloride | 151.9 |

TABLE 1-continued

| Compound Name | BP (° C.) |
|---|---|
| Methyl Ethyl Ketone Oxime | 152.0 |
| 3-Ethyl-2,5-Dimethylthiophene | 183.0 |
| 1,4-Butanediisocyanate | 230.0 |

In another embodiment, the extractive agent is at least one of the compounds listed in Table 2 below.

TABLE 2

| Compound Name | BP (° C.) |
|---|---|
| Ethanol | 78.3 |
| Isopropanol | 82.2 |
| Allyl alcohol | 97.1 |
| n-propanol | 97.2 |
| sec-butanol | 99.8 |
| isobutanol | 107.7 |
| n-butanol | 118.8 |
| 1-chloro-2-propanol | 126.5 |
| 2-chloroethanol | 128.6 |
| 2-methyl-1-butanol | 128.7 |
| isopentanol | 131.0 |
| n-pentanol | 137.8 |
| Pentafluorophenol | 145.6 |
| Cyclohexanol | 160.9 |
| 3-chloro-1-propanol | 161.0 |
| Diacetone alcohol | 167.9 |
| 1,3-dichloro-2-propanol | 174.3 |
| Phenol | 181.8 |
| m-cresol | 202.3 |
| 4-methyl-1-octanol | 204.8 |
| Benzyl alcohol | 205.5 |
| Triacetone alcohol | 212.9 |
| m-chlorophenol | 213.9 |
| p-chlorophenol | 220.0 |
| 1-decanol | 229.9 |
| 2,3-butanediol | 180.7 |
| 1,2-propylene glycol | 187.6 |
| 1,2-butanediol | 196.4 |
| Ethylene glycol | 197.3 |
| 2-methyl-2,4-pentanediol | 197.5 |
| 2,4-pentanediol | 201.0 |
| 1,3-butanediol | 208.2 |
| 3-chloro-1,2-propanediol | 213.0 |
| 1,3-propylene glycol | 214.4 |
| 2-methyl-1,3-pentanediol | 214.6 |
| trans-2-Butene-1,4-Diol | 225.9 |
| 1,4-butanediol | 228.0 |
| Dipropylene glycol | 231.8 |
| cis-2-Butene-1,4-Diol | 235.0 |
| 2-butyne-1,4-diol | 238.0 |
| 1,5-pentanediol | 239.0 |
| Diethylene glycol | 244.8 |
| 1,2-benzenediol | 245.5 |
| Glycerol (1,2,3-propanetriol) | 287.9 |
| 2-Butanone | 79.6 |
| Methyl isopropyl ketone | 94.4 |
| Methyl isopropenyl ketone | 98.0 |
| Diethyl ketone | 102.0 |
| Methyl propyl ketone | 102.3 |
| tert-butyl methyl ketone | 106.3 |
| Ethyl isopropyl ketone | 113.4 |
| Methyl isobutyl ketone | 116.0 |
| 3-methyl-2-pentanone | 117.4 |
| Ethyl-n-propylketone | 123.5 |
| Diisopropyl ketone | 124.4 |
| Diketene | 126.1 |
| Methyl-n-butyl ketone | 127.6 |
| 5-hexen-2-one | 128.5 |
| 4-methyl-3-penten-2-one | 129.8 |
| Cyclopentanone | 130.7 |
| Acetylacetone | 137.0 |
| Dipropyl ketone | 144.0 |
| Methyl isoamyl ketone | 144.8 |
| Hydroxyacetone (acetol) | 145.5 |
| Ethyl butyl ketone | 147.4 |

TABLE 2-continued

| Compound Name | BP (° C.) |
|---|---|
| Acetoin (3-hydroxybutan-2-one) | 148.0 |
| Methyl amyl ketone | 151.0 |
| Cyclohexanone | 155.4 |
| Ethyl isoamyl ketone | 158.3 |
| 4-octanone | 163.0 |
| 3-octanone | 167.5 |
| Diisobutyl ketone | 168.3 |
| Methyl hexyl ketone | 173.0 |
| Tetrahydrofurfuryl alcohol | 177.7 |
| 3-nonanone | 187.5 |
| 4-nonanone | 187.5 |
| Dibutyl ketone | 188.5 |
| Methyl heptyl ketone | 194.0 |
| Acetophenone | 202.1 |
| Isophorone | 215.2 |
| 2,6,8-trimethyl-4-nonanone | 218.3 |
| 2-hydroxyacetophenone | 221.6 |
| Dipentyl ketone | 227.4 |
| beta-Propiolactone | 162.0 |
| gamma-Butyrolactone | 204.0 |
| gamma-Valerolactone | 207.5 |
| epsilon-Caprolactone | 240.9 |
| Ethyl formate | 54.3 |
| Methyl chloroformate | 70.9 |
| n-propyl formate | 80.8 |
| tert-Butyl Formate | 82.8 |
| Ethyl chloroformate | 92.9 |
| sec-Butyl Formate | 93.4 |
| isobutyl formate | 98.1 |
| n-butyl formate | 106.1 |
| 1-phenylethyl formate | 203.9 |
| Methyl acetate | 56.9 |
| Vinyl acetate | 72.5 |
| Ethyl acetate | 77.1 |
| Isopropyl acetate | 88.5 |
| n-propyl acetate | 101.5 |
| Ethyl isobutyrate | 109.9 |
| sec-Butenyl Acetate | 112.5 |
| isobutyl acetate | 116.7 |
| n-butyl acetate | 126.1 |
| n-crotyl acetate | 130.5 |
| isopentyl acetate | 142.0 |
| Ethylchloroacetate | 144.2 |
| Methyl lactate | 144.8 |
| Isobutyl isobutyrate | 147.3 |
| Methylene glycol acetate | 151.0 |
| Ethyl lactate | 154.5 |
| 2-ethoxyethyl acetate | 156.6 |
| n-butyl n-butyrate | 165.0 |
| Dimethylmalonate | 179.4 |
| Ethyl acetoacetate | 180.8 |
| Allylidene diacetate | 184.0 |
| t-butyl acetoacetate | 184.5 |
| Diethyl oxalate | 185.5 |
| n-butyl valerate | 186.5 |
| Ethylene glycol diacetate | 190.5 |
| 2-butoxyethylacetate | 192.0 |
| Isopentyl isovalerate | 194.0 |
| Dimethyl succinate | 196.2 |
| Diethyl malonate | 198.9 |
| Methyl benzoate | 199.5 |
| Dimethyl maleate | 205.0 |
| Ethyl benzoate | 213.4 |
| Diethyl succinate | 217.0 |
| Methyl 4-methylbenzoate | 217.0 |
| Methyl salicylate | 220.8 |
| Diethyl maleate | 225.0 |
| Methyl decanoate | 231.9 |
| isopropyl acrylate | 110.0 |
| Ethyl methacrylate | 117.0 |
| Propyl methacrylate | 140.9 |
| isobutyl methacrylate | 155.0 |
| Butyl methacrylate | 163.0 |
| Ethylene glycol monoacrylate | 210.9 |
| 2-ethylhexyl acrylate | 216.0 |
| 2-hydroxyethyl methacrylate | 226.0 |
| n-butyl isocyanate | 115.0 |
| Phenyl isocyanate | 166.3 |

TABLE 2-continued

| Compound Name | BP (° C.) |
|---|---|
| Nitric acid | 83.0 |
| Formic acid | 100.6 |
| Acetic acid | 117.9 |
| Acetic anhydride | 139.6 |
| Propionic anhydride | 167.0 |
| Isobutyric anhydride | 182.5 |
| Butyric anhydride | 197.8 |
| Maleic anhydride | 202.0 |
| Acetoacetic acid | 205.1 |
| Methoxyacetic acid | 205.1 |
| Methyl maleic anhydride | 213.0 |
| Isobutyraldehyde | 64.1 |
| Methacrolein | 68.0 |
| Butyraldehyde | 74.8 |
| Chloroacetaldehyde | 84.9 |
| cis-crotonaldehyde | 88.7 |
| Dichloroacetaldehyde | 88.9 |
| 2-methylbutyraldehyde | 91.7 |
| 3-methylbutyraldehyde | 92.5 |
| trans-crotonaldehyde | 102.5 |
| Pentanal | 102.0 |
| Hexanal | 128.0 |
| 2-methyl-2-pentenal | 136.5 |
| Hydroxyacetaldehyde | 150.0 |
| Heptanal | 153.0 |
| 2-methylheptanal | 156.0 |
| 4-hydroxybutyraldehyde | 158.9 |
| Cyclohexanealdehyde | 159.3 |
| Furfural | 161.7 |
| 2-ethylhexanal | 163.0 |
| 3-hydroxy-2-methyl propionaldehyde | 166.9 |
| 3-hydroxybutyraldehyde | 170.9 |
| Octanal | 172.0 |
| Benzaldehyde | 178.8 |
| 3-ethyl heptanal | 180.4 |
| 2-methyl octanal | 186.9 |
| Glutaraldehyde | 188.0 |
| Nonanal | 192.4 |
| 2-hydroxybenzaldehyde | 196.5 |
| 2-phenylpropionaldehyde | 198.9 |
| 3-methylbenzaldehyde | 199.0 |
| 2-methylbenzaldehyde | 201.0 |
| 4-methylbenzaldehyde | 207.3 |
| Decanal | 208.5 |
| Undecanal | 233.0 |
| Dodecanal | 248.9 |
| 1,2-butylene oxide | 63.4 |
| Tetrahydrofuran | 66.0 |
| 1,2-dimethoxyethane | 84.6 |
| Dipropyl ether | 90.1 |
| 1,3-dioxane | 105.0 |
| Methoxyacetone | 114.5 |
| Trioxane | 114.5 |
| 1-chloro-2,3-epoxypropane | 118.5 |
| Propylene glycol monomethyl ether | 120.1 |
| 2-methoxyethanol | 124.5 |
| 2-ethoxyethanol | 135.0 |
| 1-isopropoxy-2-propanol | 138.0 |
| Dibutyl ether | 141.0 |
| Ethylene glycol monopropyl ether | 151.4 |
| Propylene glycol 1-tert-butyl ether | 152.1 |
| Propanediol monomethyl ether propionate | 157.0 |
| Diethylene glycol dimethyl ether | 162.5 |
| Propylene glycol ethyl ether acetate | 164.9 |
| 2-butoxyethanol | 171.3 |
| Dichloroethyl ether | 178.5 |
| Ethylene glycol monocrotyl ether | 180.0 |
| 2-pentoxyethanol | 187.5 |
| Dipropylene glycol monomethyl ether | 188.3 |
| Diethylene glycol monomethyl ether | 193.6 |
| Diethylene glycol monoethyl ether | 201.9 |
| 2-methoxyphenol | 205.0 |
| Ethylene glycol monohexyl ether | 208.3 |
| Diethylene glycol ethyl ether acetate | 214.9 |
| Triethylene glycol dimethyl ether | 216.0 |
| Diethylene glycol monobutyl ether | 231.0 |
| Dipropylene glycol n-butyl ether | 231.7 |
| Dipropylene glycol t-butyl ether | 241.9 |
| Tripropylene glycol monomethyl ether | 242.4 |
| Diethylene glycol monobutyl ether acetate | 245.3 |
| Propylene glycol monomethyl ether | Unknown |
| Nitromethane | 101.2 |
| Nitroethane | 114.1 |
| 2-nitropropane | 120.3 |
| 1-nitropropane | 131.2 |
| 1-nitrobutane | 152.8 |
| Nitrobenzene | 210.8 |
| o-nitrotoluene | 222.5 |
| m-nitrotoluene | 231.9 |
| 1-chloro-3-nitrobenzene | 235.7 |
| p-nitrotoluene | 238.5 |
| 1-chloro-2-nitrobenzene | 245.9 |
| Acrylonitrile | 77.3 |
| Acetonitrile | 81.7 |
| Methacrylonitrile | 90.3 |
| Propionitrile | 97.1 |
| Isobutyronitrile | 103.6 |
| cis-Crotonitrile | 107.5 |
| Butyronitrile | 117.6 |
| Vinylacetonitrile | 118.5 |
| trans-Crotonitrile | 121.2 |
| Cyclopropanenitrile | 135.0 |
| Valeronitrile | 141.6 |
| Aminoacetonitrile | 151.9 |
| Hexanenitrile | 163.5 |
| 2-hydroxy-2-methylpropionitrile | 170.9 |
| 2-hydroxy-3-butenenitrile | 187.9 |
| Benzonitrile | 191.0 |
| Nicotinonitrile | 201.0 |
| Methyl cyanoacetate | 205.1 |
| Ethyl cyanoacetate | 206.0 |
| Malononitrile | 218.4 |
| Maleonitrile (cis-2-butenedinitrile) | 218.9 |
| 3-hydroxypropionitrile | 221.0 |
| Aminocapronitrile | 229.9 |
| Benzyl nitrile | 233.5 |
| N,N-dimethylformamide | 152.0 |
| Trifluoroacetamide | 162.5 |
| N,N-dimethylacetamide | 166.1 |
| N-methylformamide | 199.5 |
| tert-Butylformamide | 202.0 |
| N-methylacetamide | 205.0 |
| Formamide | 219.9 |
| Acetamide | 221.2 |
| Chloromethyl sulfone | 161.5 |
| Ethanesulfonyl chloride | 175.3 |
| Dimethyl sulfoxide | 190.9 |
| Chloropropylsulfone | 197.5 |
| Dimethyl sulfone | 249.5 |
| Sulfolene | 249.9 |
| 3-methyl sulfolane | 276.0 |
| Sulfolane | 287.3 |
| Propyleneimine | 66.5 |
| Dimethylethanolamine | 134.0 |
| Methylethanolamine | 158.0 |
| Diethylethanolamine | 163.0 |
| Aniline | 184.0 |
| 2-piperazinylethylamine | 220.1 |
| m-chloroaniline | 228.5 |
| p-chloroaniline | 230.5 |
| Quinoline | 237.2 |
| Isoquinoline | 243.2 |
| Methyl diethanolamine | 247.6 |
| Isoxazole | 94.8 |
| N-methylpyrrole | 112.7 |
| Pyridine | 115.3 |
| 2-methylpyridine | 129.4 |
| 3-methylpyridine | 144.1 |
| 4-methylpyridine | 145.4 |
| 2,4,6-trimethylpyridine | 170.6 |
| Pyrazole | 187.0 |
| N-methyl-2-pyrrolidone | 204.3 |
| Pyridazine | 208.0 |
| N-ethyl-2-pyrrolidone | 218.0 |
| 1,3-dimethyl-2-imidazolidinone | 221.0 |

TABLE 2-continued

| Compound Name | BP (° C.) |
|---|---|
| 4-formylmorpholine | 240.0 |
| 2-pyrrolidone | 251.2 |
| Ethyl phenyl carbonate | 226.0 |
| Vinylethylene carbonate | 238.6 |
| Propylene carbonate | 241.7 |
| Ethylene carbonate | 248.2 |
| Trimethyl phosphate | 197.2 |
| Triethyl phosphate | 215.0 |
| Tri-n-butyl phosphate | 289.0 |
| Ethyl methyl disulfide | 134.0 |
| Ethyl propyl disulfide | 173.7 |
| Ethyl-tert-butyl disulfide | 175.7 |
| Di-n-butyl disulfide | 236.0 |
| Diethylsulfite | 158.0 |
| Dimethyl sulfate | 189.0 |
| Diethyl sulfate | 209.5 |
| Vinyltrichlorosilane | 90.7 |
| Methyl vinyl dichlorosilane | 93.8 |
| Ethyltrichlorosilane | 97.9 |
| (3,3,3-trifluoropropyl)methyldichlorosilane | 122.2 |
| Dichlorodiethylsilane | 130.0 |
| (3-chloropropyl)-dimethylchlorosilane | 179.0 |
| Trichloro(3-chloropropyl)silane | 182.3 |
| (3-chloropropyl) trimethoxysilane | 199.0 |
| Phenyltrichlorosilane | 201.8 |
| Phenylmethyldichlorosilane | 204.2 |
| gamma-Aminopropyltriethoxysilane | 219.9 |
| Triacetoxy methylsilane | 220.0 |
| Triacetoxy ethylsilane | 227.0 |
| 3-(triethoxysilyl)propionitrile | 238.9 |
| Phosphorus oxychloride | 105.5 |
| Methylgermanium trichloride | 111.0 |
| Ethyl thiolacetate | 114.9 |
| 3-(methylmercapto)propanal | 165.5 |
| Ethylene glycol dinitrate | 199.0 |
| Hexamethyl phosphoramide | 233.0 |
| 1,1-Dichloroethane | 57.3 |
| cis-1,2-Dichloroethylene | 60.5 |
| 2-chlorobutane | 68.1 |
| Isobutyl chloride | 68.9 |
| n-propyl bromide | 71.0 |
| Trifluoroacetic acid | 71.8 |
| 1,1,1-Trichloroethane | 74.1 |
| 1-chlorobutane | 78.4 |
| Fluorobenzene | 84.7 |
| 1,1-Dichloropropane | 88.1 |
| 2-bromobutane | 91.2 |
| 2,3-dichloropropene | 93.4 |
| 1,2-difluorobenzene | 93.9 |
| 1,2-Dichloropropane | 96.4 |
| n-butyl bromide | 101.3 |
| (Trifluoromethyl)benzene | 102.1 |
| n-propyl iodide | 102.5 |
| cis-1,3-Dichloropropene | 104.3 |
| Chloroacetyl chloride | 106.0 |
| 1-chloropentane | 107.5 |
| 1,1-dibromoethane | 108.0 |
| trans-1,3-Dichloropropene | 112.0 |
| 3,4-dichloro-1-butene | 114.9 |
| 1,3-Dichloropropane | 120.4 |
| 1,2-dichlorobutane | 124.0 |
| 1,3-dichloro-trans-2-butene | 128.0 |
| 2,3,3,3-tetrachloropropene | 128.0 |
| n-butyl iodide | 130.6 |
| Chlorobenzene | 131.7 |
| Chlorocyclohexane | 142.9 |
| 1,1,2,2-tetrachloroethane | 145.1 |
| 1,4-dichlorobutane | 155.1 |
| 1,2,3-Trichloropropane | 156.9 |
| 1,1,1,3-tetrachloropropane | 159.0 |
| p-chlorotoluene | 162.5 |
| 1,1,2,3-tetrachloropropene | 166.0 |
| 1-bromoheptane | 178.8 |
| o-dichlorobenzene | 180.4 |
| 1,5-dichloropentane | 183.0 |
| 1,1,1,3-tetrachloropropane | 183.7 |
| 4-chloro-1,2-dimethylbenzene | 192.5 |
| 1,1,1,2,3-pentachloropropane | 193.0 |
| Benzoyl chloride | 197.0 |
| 1,1,1,3,3,3-hexachloropropane | 210.1 |
| Benzotrichloride | 213.5 |
| Dichloromethyl benzene | 213.9 |
| 1,2,3-trichlorobenzene | 218.6 |
| m-chlorobenzoyl chloride | 224.9 |

The extractive agents according to the present invention may be used alone or in combination with each other as the extractive agents for the separation. In either case, the extractive agent increases or decreases the volatility of cis-HFO-1336mzz or at least one chlorofluoroolefin relative to each other.

By conventional distillation is meant distillation in which the components of a mixture are separated based solely on differences in their relative volatilities and where no additional chemical compounds are added to facilitate the separation.

By extractive distillation is meant a process in which an extractive agent is introduced at an upper feed point of a distillation column, whereas the mixture requiring separation is introduced at the same point or preferably, at a relatively lower feed point of the column. The substantially liquid extractive agent passes downwardly through trays or packing in the column and exits the column bottoms with one or more components of the mixture to be separated. While in the presence of the extractive agent, at least one of the components of an initial mixture to be separated becomes relatively more volatile compared to the other components of the mixture, resulting in this more volatile component of the initial mixture exiting the column overheads. Extractive distillation may be employed when the components of a mixture form an azeotrope or otherwise have close relative volatilities that do not afford effective separation of the components by conventional distillation. In the case of the separation of cis-HFO-1336mzz and trans-HCFC-1326mxz, the two components form a minimum boiling azeotrope with a composition of approximately 56.8 mole percent (52.1 weight percent) cis-HFO-1336mzz and a boiling point of 32.1° C. at 1 atmosphere pressure. In the case of the separation of cis-HFO-1336mzz and cis-HCFC-1326mxz, the two components form azeotrope-like compositions at one atmosphere pressure from 0.1 to 17.4 mole percent cis-HFO-1336mzz and from 43.0 to 99.9 mole percent cis-HFO-1336mzz. In the case of the separation of cis-HFO-1336mzz and CFC-1317mx, the two components form a minimum boiling azeotrope with a composition of approximately 41.0 mole percent cis-HFO-1336mzz and a boiling point of 28.9° C. at 1 atmosphere pressure. In extractive distillation, at least one extractive agent is used which causes the relative volatilities of the components in a mixture to be altered such that the resultant relative volatilities, i.e., that of components of the mixture in the presence of the extractive agent, become sufficiently different to permit separation of the components by distillation techniques.

The relative volatility of two chemical compounds in a mixture is the ratio of the vapor-phase mole fraction of the first compound divided by its equilibrium liquid-phase mole friction to the vapor-phase mole fraction of the second compound divided by its equilibrium liquid-phase mole fraction. The ratio of a compound's equilibrium vapor-phase mole fraction to its liquid-phase mole fraction is commonly called its K-value. Thus, the relative volatility of two compounds is simply the ratio of their K-values. In one embodiment, the relative volatility of cis-HFO-1336mzz in a mixture with trans-HCFC-1326mxz is the ratio of the vapor phase mole fraction of cis-HFO-1336mzz divided the liquid phase mole fraction of cis-HFO-1336mzz to the vapor phase mole fraction of trans-HCFC-1326mxz divided by the liquid phase mole fraction of trans-HCFC-1326mxz. In another embodiment, the relative volatility of cis-HFO-1336mzz in a mixture with cis-HCFC-1326mxz is the ratio of the vapor phase mole fraction of cis-HFO-1336mzz divided the liquid mole fraction of cis-HFO-1336mzz to the vapor phase mole fraction of cis-HCFC-1326mxz divided the liquid phase mole fraction of cis-HCFC-1326mxz. In yet another embodiment, the relative volatility of cis-HFO-1336mzz in a mixture with CFC-1317mx is the ratio of the vapor phase mole fraction of cis-HFO-1336mzz divided the liquid phase mole fraction of cis-HFO-1336mzz to the vapor phase mole fraction of CFC-1317mx divided the liquid phase mole fraction of CFC-1317mx.

To determine the relative volatility of a given compound in a mixture with another compound, a method known as the PTx Method may be used. In this procedure, the total absolute pressure in a cell of known volume is measured at a constant temperature for various compositions of the two compounds. More specifically, a known amount of the first component is charged to the cell, the system is allowed equilibrate as the cell is held at constant temperature, and then the cell pressure is measured. A known amount of the second component is then added to the cell, the system is again allowed to equilibrate, and the cell pressure is measured. This process is repeated with known incremental amounts of the second component added and the pressure measured each time. Often when the total amount of the second component added is roughly equal to the amount of the first component initially charged, the cell is emptied and the process is repeated with a known amount of the second component charged to the cell followed by the addition of known incremental amounts of the first component with the equilibrated cell pressure measured at each step.

The measured PTx data can be converted into equilibrium vapor and liquid phase compositions by using an activity coefficient model, such as the Wilson equation, the Non-Random Two-Liquid (NRTL) equation, the Universal Quasi Chemical (UNIQUAC) equation, the Margules equation, or the van Laar equation, to represent liquid phase nonidealities in the well known "gamma/phi" approach to vapor-liquid equilibrium. In this approach, the equilibrium vapor and liquid phases in an n-component mixture are related by:

$$y_i P = x_i \gamma_i P_i^{vp} \Phi_i \text{ for } i=1,2,\ldots n \quad (1)$$

where
 $y_i$ is the vapor-phase mole fraction of component i,
 $x_i$ is the liquid-phase mole fraction of component i,
 P is the total system pressure,
 $P_i^{vp}$ is the vapor pressure of component i at the system temperature,
 $\gamma_i$ is the liquid-phase activity coefficient of component i, $$\Phi_i = (\phi_i^s/\phi_i^v) Poy_i \quad (2)$$

$\phi_i^v$ is the vapor-phase fugacity coefficient of component i,
 $\phi_i^s$ is the fugacity coefficient of component i at saturation conditions,
 $Poy_i$ is the Poyntinq correction for component i defined as:

$$POy_i = \exp \int_{P_i^{vp}}^{P} \frac{V_i^L dP}{RT} \quad (3)$$

$V_i^L$ is the molar liquid volume of component i, which can usually be treated as constant so the integral is easily evaluated,
 R is the gas constant, and
 T is the absolute system temperature.

The fugacity coefficients can be calculated from any suitable equation of state. At low pressures the magnitude of $\Phi_i$ is often near unity. Consequently, at such pressures (up to several atmospheres), setting $\Phi_i=1$ can greatly simplify the calculations without a significant loss of accuracy.

In practice, the parameters in the chosen activity coefficient equation are adjusted until they enable the experimental data to be accurately reproduced by Equation 1. This is commonly achieved using Barker's method, which minimizes the deviation between the calculated and measured pressures. The so obtained activity coefficient equation parameters can then be used with Equation 1 to calculate vapor-liquid phase equilibrium at other conditions.

Without wishing to be bound by any theory or explanation, it is believed that the NRTL equation, together with the PTx cell data, can sufficiently predict the relative volatility of cis-HFO-1336mzz and at least one chlorofluoroolefin, and can therefore predict the behavior of cis-HFO-1336mzz and at least one chlorofluoroolefin in multi-stage separation equipment such as distillation columns. Thus, it is believed that the NRTL equation, together with the PTx cell data, can sufficiently predict the relative volatility of cis-HFO-1336mzz and trans-HCFC-1326mxz, and can therefore predict the behavior of cis-HFO-1336mzz and trans-HCFC-1326mxz in multi-stage separation equipment such as distillation columns. Similarly, the relative volatility of cis-HFO-1336mzz and cis-HCFC-1326mxz and of cis-HFO-1336mzz and CFC-1317mx can be predicted and their behavior in multi-stage separation equipment predicted.

The results of PTx measurements and the above calculations indicate that cis-HFO-1336mzz and trans-HCFC-1326mxz form a minimum-boiling azeotrope with a composition of approximately 56.8 mole percent (52.1 weight percent) cis-HFO-1336mzz and a boiling point of 32.1° C. at atmospheric pressure. Because the vapor and liquid compositions of an azeotrope are identical, the relative volatility of cis-HFO-1336mzz and trans-HCFC-1326mxz is equal to 1 at the azeotropic composition. Thus it is not possible to completely separate cis-HFO-1336mzz from trans-HCFC-1326mxz by conventional distillation.

In another embodiment, the results of PTx measurements and the above calculations indicate that cis-HFO-1336mzz and cis-HCFC-1326mxz form azeotrope-like compositions from 0.1 to 17.4 mole percent cis-HFO-1336mzz and from 43.0 to 99.9 mole percent cis-HFO-1336mzz at atmospheric pressure. Thus it would be difficult to completely separate cis-HFO-1336mzz from cis-HCFC-1326mxz by conventional distillation.

In another embodiment, the results of PTx measurements and the above calculations indicate that cis-HFO-1336mzz and CFC-1317mx form a minimum-boiling azeotrope with a composition of approximately 41.0 mole percent (34.5 weight percent) cis-HFO-1336mzz and a boiling point of 28.9° C. at atmospheric pressure. Because the vapor and liquid compositions of an azeotrope are identical, the relative volatility of cis-HFO-1336mzz and CFC-1317mx is equal to 1 at the azeotropic composition. Thus it is not possible to completely separate cis-HFO-1336mzz from CFC-1317mx by conventional distillation.

Extractive agents work by altering the liquid-phase activity coefficients of the chemical compounds being separated. A common measure of the effectiveness of a given extractive agent is its selectivity, which is defined as the ratio of the liquid-phase activity coefficients of the compounds being separated in the presence of the extractive agent. The farther the selectivity is from unity, the more effective the extractive agent is. Most commonly, the selectivity is determined under conditions where the extractive agent concentration is so large that the concentration of each of the compounds being separated approaches infinite dilution. The infinite-dilution selectivity is the ratio of the infinite-dilution activity coefficients of the compounds being separated measured or calculated in the presence of an extractive agent. As used herein, the term selectivity is to be interpreted as the infinite-dilution selectivity.

The selectivities resulting from PTx measurements and the aforementioned calculations for cis-HFO-1336mzz and trans-HCFC-1326mxz in the presence of various extractive agents are summarized in Table 3.

Shown are the selectivities of cis-HFO-1336mzz relative to trans-HCFC-1326mxz at 40° C. where both cis-HFO-1336mzz and trans-HCFC-1326mxz are at infinite dilution in the listed extraction agent.

TABLE 3

| Extractive agent | Selectivity 1336/trans-1326 |
| --- | --- |
| n-Octane | 2.06 |
| Perchloroethylene | 2.03 |
| Toluene | 0.91 |
| n-Butanol | 0.61 |
| Tetrahydrofuran | 0.57 |
| Ethyl Acetate | 0.48 |
| 2-Butanone | 0.45 |
| N,N-dimethylformamide | 0.31 |

As shown above in Table 3, the present inventors have found that the relative volatilities of cis-HFO-1336mzz to trans-HCFC-1326mxz can be increased or decreased in the presence of different extractive agents. Selectivity values greater than unity denote extractive agents which increase the volatility of cis-HFO-1336mzz relative to trans-HCFC-1326mxz. Selectivity values less than unity denote extractive agents which have the opposite effect. For example, for tetrahydrofuran specifically, the volatility of trans-HCFC-1326mxz is increased with respect to the volatility of cis-HFO-1336mzz. This discovery that extractive agents can alter the relative volatility between cis-HFO-1336mzz and trans-HCFC-1326mxz allows for separation of cis-HFO-1336mzz from a first mixture comprising cis-HFO-1336mzz and trans-HCFC-1326mxz by extractive distillation in the presence of an appropriate extractive agent. One type of appropriate extractive agent for a first mixture comprising cis-HFO-1336mzz and trans-HCFC-1326mxz is one which causes the relative volatility of cis-HFO-1336mzz to trans-HCFC-1326mxz to be greater than 1.2, with the cis-HFO-1336mzz being more volatile, thus permitting cis-HFO-1336mzz to be removed from the top of the distillation zone and trans-HCFC-1326mxz to be removed from the bottom of the distillation zone together with the extractive agent. Another type of appropriate extractive agent for a first mixture comprising cis-HFO-1336mzz and trans-HCFC-1326mxz is one which causes the relative volatility of cis-HFO-1336mzz to trans-HCFC-1326mxz to be less than 0.8, with the cis-HFO-1336mzz being less volatile, thus permitting trans-HCFC-1326mxz to be recovered from the top of the distillation zone and cis-HFO-1336mzz to be removed from the bottom of the distillation zone together with the extractive agent. In order for an extractive agent to be effective in separating cis-HFO-1336mzz from trans-HCFC-1326mxz by extractive distillation, the relative volatility of cis-HFO-1336mzz to trans-HCFC-1326mxz in the presence of the extractive agent is greater than about 1.2 or less than about 0.8. In another embodiment, the relative volatility of cis-HFO-1336mzz to trans-HCFC-1326mxz in the presence of the extractive agent is greater than about 1.5 or less than about 0.7. In yet another embodiment, it is greater than about 2.0 or less than about 0.5.

In one embodiment of this invention, trans-HCFC-1326mxz becomes more volatile than cis-HFO-1336mzz in the presence of the extractive agent, and is removed from the top of the distillation column. cis-HFO-1336mzz is recovered as a bottoms product together with the extractive agent.

In another embodiment of this invention, cis-HFO-1336mzz becomes more volatile than trans-HCFC-1326mxz in the presence of the extractive agent, and is recovered substantially free of trans-HCFC-1326mxz from the top of the distillation column. trans-HCFC-1326mxz is removed from the bottom of the distillation column together with the extractive agent.

The selectivities resulting from PTx measurements and the aforementioned calculations for cis-HFO-1336mzz and cis-HCFC-1326mxz in the presence of various extractive agents are summarized in Table 4.

Shown are the selectivities of cis-HFO-1336mzz relative to cis-HCFC-1326mxz at 40° C. where both cis-HFO-1336mzz and cis-HCFC-1326mxz are at infinite dilution in the listed extraction agent.

TABLE 4

| Extractive agent | Selectivity 1336/cis-1326 |
| --- | --- |
| Perchloroethylene | 2.48 |

Similarly, the present inventors have found that the relative volatilities of cis-HFO-1336mzz to cis-HCFC-1326mxz can be increased or decreased in the presence of different extractive agents. Selectivity values greater than unity denote extractive agents which increase the volatility of cis-HFO-1336mzz relative to cis-HCFC-1326mxz. One type of appropriate extractive agent for a first mixture comprising cis-HFO-1336mzz and cis-HCFC-1326mxz is one which causes the relative volatility of cis-HFO-1336mzz to cis-HCFC-1326mxz to be greater than 1.2, with the cis-HFO-1336mzz being more volatile, thus permitting cis-HFO-1336mzz to be removed from the top of the distillation zone and cis-HCFC-1326mxz to be removed from the bottom of the distillation zone together with the extractive agent.

In one embodiment of this invention, cis-HCFC-1326mxz becomes more volatile than cis-HFO-1336mzz in the presence of the extractive agent, and is removed from the top of the distillation column. cis-HFO-1336mzz is recovered as a bottoms product together with the extractive agent.

In another embodiment of this invention, cis-HFO-1336mzz becomes more volatile than cis-HCFC-1326mxz in the presence of the extractive agent, and is recovered substantially free of cis-HCFC-1326mxz from the top of the distillation column. cis-HCFC-1326mxz is removed from the bottom of the distillation column together with the extractive agent.

The selectivities resulting from PTx measurements and the aforementioned calculations for cis-HFO-1336mzz and CFC-1317mx in the presence of various extractive agents are summarized in Table 5.

Shown are the selectivities of cis-HFO-1336mzz relative to CFC-1317mx at 40° C. where both cis-HFO-1336mzz and CFC-1317mx are at infinite dilution in the listed extraction agent.

TABLE 5

| Extractive agent | Selectivity 1336/1317mx |
| --- | --- |
| Perchloroethylene | 1.60 |

Similarly, the present inventors have found that the relative volatilities of cis-HFO-1336mzz to CFC-1317mx can be increased or decreased in the presence of different extractive agents. Selectivity values greater than unity denote extractive agents which increase the volatility of cis-HFO-1336mzz relative to CFC-1317mx. One type of appropriate extractive agent for a first mixture comprising cis-HFO-1336mzz and CFC-1317mx is one which causes the relative volatility of cis-HFO-1336mzz to CFC-1317mx to be greater than 1.2, with the cis-HFO-1336mzz being more volatile, thus permitting cis-HFO-1336mzz to be removed from the top of the distillation zone and CFC-1317mx to be removed from the bottom of the distillation zone together with the extractive agent.

In one embodiment of this invention, CFC-1317mx becomes more volatile than cis-HFO-1336mzz in the presence of the extractive agent, and is removed from the top of the distillation column. cis-HFO-1336mzz is recovered as a bottoms product together with the extractive agent.

In another embodiment of this invention, cis-HFO-1336mzz becomes more volatile than CFC-1317mx in the presence of the extractive agent, and is recovered substantially free of CFC-1317mx from the top of the distillation column. CFC-1317mx is removed from the bottom of the distillation column together with the extractive agent.

In the extractive distillation process, the extractive agent is preferably recovered and recycled. For instance, for extractive agents that cause trans-HCFC-1326mxz to be more volatile than cis-HFO-1336mzz, the extractive agent will be recovered from the bottom of the extraction column together with cis-HFO-1336mzz, and may be further purified in a conventional distillation column and recycled to the first contacting step.

In one embodiment of this invention, the first mixture contains more than about 50 wt % of cis-HFO-1336mzz and the trans-HCFC-1326mxz content is less than about 50 wt %.

In another embodiment of this invention, the first mixture contains more than about 70 wt % of cis-HFO-1336mzz and the trans-HCFC-1326mxz content is less than about 30 wt %.

In another embodiment of this invention, the first mixture contains more than about 90 wt % of cis-HFO-1336mzz and the trans-HCFC-1326mxz content is less than about 10 wt %.

In another embodiment of this invention, the first mixture contains more than about 99 wt % of cis-HFO-1336mzz and the trans-HCFC-1326mxz content is less than about 1 wt %.

According to the present invention, cis-HFO-1336mzz containing less than 1000 ppm of trans-HCFC-1326mxz may be produced. Further, cis-HFO-1336mzz containing less than 100 ppm of trans-HCFC-1326mxz, and further cis-HFO-1336mzz containing less than 10 ppm of trans-HCFC-1326mxz, and even further cis-HFO-1336mzz containing less than 1 ppm of trans-HCFC-1326mxz may be produced.

According to the present invention, cis-HFO-1336mzz containing less than 1000 ppm of cis-HCFC-1326mxz may be produced. Further, cis-HFO-1336mzz containing less than 100 ppm of cis-HCFC-1326mxz, and further cis-HFO-1336mzz containing less than 10 ppm of cis-HCFC-1326mxz, and even further cis-HFO-1336mzz containing less than 1 ppm of cis-HCFC-1326mxz may be produced.

Also according to the present invention, cis-HFO-1336mzz containing less than 1000 ppm of chlorofluoroolefins may be produced. Further, cis-HFO-1336mzz containing less than 100 ppm of chlorofluoroolefins may be produced, and further, cis-HFO-1336mzz containing less than 10 ppm of chlorofluoroolefins may be produced and, even further, cis-HFO-1336mzz containing less than 1 ppm of chlorofluoroolefins may be produced.

In one embodiment of the present process, an extractive agent is introduced at an upper feed point of an extractive distillation column, whereas the first mixture comprising cis-HFO-1336mzz and trans-HCFC-1326mxz is introduced at a relatively lower point in the column. The extractive agent passes downwardly through trays or packing in the column and contacts the first mixture thereby forming a second mixture. While in the presence of an extractive agent such as without limitation N—N-dimethyl formamide, ethyl acetate, 2-butanone, tetrahydrofuran or n-butanol, trans-HCFC-1326mxz is made relatively more volatile than cis-HFO-1336mzz, thereby causing an overhead stream containing enriched trans-HCFC-1326mxz to exit the top of the column. Such overhead stream exiting the top of the column can be condensed by reflux condensers. At least a portion of this condensed overhead stream can be returned to the top of the column as reflux, and the remainder is either removed as waste or recovered as product. The extractive agent and cis-HFO-1336mzz substantially free of trans-HCFC-1326mxz comprise a third mixture that exits from the bottom of the column, which can then be passed to a stripper or distillation column for separation by conventional distillation or other known methods. The extractive agent can be recycled to the extractive distillation column.

In another embodiment, while in the presence of an extractive agent such as without limitation octane or perchloroethylene, cis-HFO-1336mzz is relatively more volatile than trans-HCFC-1326mxz, thereby causing an overhead stream containing concentrated cis-HFO-1336mzz to exit the top of the column. Such overhead stream exiting the top of the column can be condensed by reflux condensers. At least a portion of this condensed overhead stream can be returned to the top of the column as reflux, and the remainder is recovered as product. The extractive agent and trans-HCFC-1326mxz comprise a third mixture that exits from the bottom of the column, which can then be passed to a stripper or distillation column for separation by conventional distillation or other known methods. The extractive agent can be recycled to the extractive distillation column.

In yet another embodiment, while in the presence of an extractive agent such as without limitation octane or perchloroethylene, cis-HFO-1336mzz is relatively more volatile than cis-HCFC-1326mxz, thereby causing an overhead stream containing concentrated cis-HFO-1336mzz to exit the top of the column. Such overhead stream exiting the top of the column can be condensed by reflux condensers. At least a portion of this condensed overhead stream can be returned to the top of the column as reflux, and the remainder is recovered as product. The extractive agent and cis-HCFC-1326mxz comprise a third mixture that exits from the bottom of the column, which can then be passed to a stripper or distillation column for separation by conventional distillation or other known methods. The extractive agent can be recycled to the extractive distillation column.

In yet another embodiment, while in the presence of an extractive agent such as without limitation octane or perchloroethylene, cis-HFO-1336mzz is relatively more volatile than CFC-1317mx, thereby causing an overhead stream containing concentrated cis-HFO-1336mzz to exit the top of the column. Such overhead stream exiting the top of the column can be condensed by reflux condensers. At least a portion of this condensed overhead stream can be returned to the top of the column as reflux, and the remainder is recovered as product. The extractive agent and CFC-1317mx comprise a third mixture that exits from the bottom of the column, which can then be passed to a stripper or distillation column for separation by conventional distillation or other known methods. The extractive agent can be recycled to the extractive distillation column.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Examples 1-10

Infinite Dilution Selectivity with Various Solvents as the Extractive Agent

The selectivity for this example is defined as the infinite-dilution activity coefficient of cis-HFO-1336mzz in solvent at 40° C. divided by the infinite-dilution activity coefficient of trans-HCFC-1326mxz, cis-HCFC-1326mxz or CFC-1317mx in the same solvent at 40° C. where the infinite-dilution activity coefficients were calculated from NRTL model parameters regressed from measured PTx data. This same selectivity definition will be used in the next examples as well.

TABLE 6

| Solvent | Selecitivity cis-1336mzz/trans-1326mxz |
|---|---|
| Toluene | 0.91 |
| n-octane | 2.06 |
| n-butanol | 0.61 |
| Ethyl acetate | 0.48 |
| N,N-dimethylformamide | 0.31 |
| Tetrahydrofuran | 0.57 |
| 2-butanone | 0.45 |
| perchloroethylene | 2.03 |
| | Selecitivity cis-1336mzz/cis-1326mxz |
| perchloroethylene | 2.48 |
| | Selecitivity cis-1336mzz/1317mx |
| perchloroethylene | 1.60 |

Example 11

A room temperature, 50/50 wt % mixture of cis-HFO-1336mzz and trans-HCFC-1326mxz are fed via stream 100 to the tenth theoretical stage from the bottom of distillation column 101 of FIG. 1. The extractive agent feed stream, comprising essentially of n-octane, is fed via stream 102 to the tenth theoretical stage from the top of column 101. The molar flow rate of stream 102 is set to eight times the molar flow rate of stream 100. Distillation column 101 contains 50 theoretical stages and operates with a top pressure of approximately 5 psig and with a mass reflux flow rate (stream 104) that is twice the flow rate of stream 100. Distillate stream 105, consisting predominantly of cis-HFO-1336mzz, is removed from the top of column 101. The bottoms stream withdrawn from the bottom of 101 via stream 109 contains most of the trans-HCFC-1326mxz and only a small fraction of the cis-HFO-1336mzz fed to 101 via 100. Table 7 shows the compositions of the streams entering and leaving column 101. The concentration of cis-HFO-1336mzz in stream 105 is far in excess of the cis-HFO-1336mzz concentration in the azeotrope formed by cis-HFO-1336mzz and trans-HCFC-1326mxz and the concentration of cis-HFO-1336mzz on an n-octane-free basis in stream 109 is far below its azeotropic concentration, demonstrating that n-octane has enabled azeotrope-forming mixtures of cis-HFO-1336mzz and trans-HCFC-1326mxz to be effectively separated.

TABLE 7

| | 100 | 102 | 105 | 109 |
|---|---|---|---|---|
| MASS FRACTIONS | | | | |
| cis-HFO-1336mzz | 0.5000 | 0 | 0.9969 | 280 ppm |
| trans-HCFC-1326mxz | 0.5000 | 0 | 0.0030 | 0.0892 |
| n-Octane | 0 | 1.0000 | 70 ppm | 0.9105 |
| TOTAL FLOW: | | | | |
| lb-mole/hr | 0.5567 | 4.4533 | 0.3046 | 4.7053 |
| lb/hr | 100.0000 | 508.6709 | 50.0000 | 558.6709 |
| STATE VARIABLES: | | | | |
| Temperature C. | 25.0 | 50.0 | 41.5 | 106.0 |
| Pressure psia | 24.7 | 24.7 | 19.6 | 20.1 |

Example 12

A room temperature, 50/25/25 wt % mixture of cis-HFO-1336mzz, cis-HCFC-1326mxz and trans-HCFC-1326mxz are fed via stream 100 to the tenth theoretical stage from the bottom of distillation column 101 of FIG. 1. The extractive agent feed stream, comprising essentially of perchloroethylene (PCE), is fed via stream 102 to the tenth theoretical stage from the top of column 101. The molar flow rate of stream 102 is set to ten times the molar flow rate of stream 100. Distillation column 101 contains 50 theoretical stages and operates with a top pressure of approximately 5 psig and with a mass reflux flow rate (stream 104) that is twice the flow rate of stream 100. Distillate stream 105, consisting predominantly of cis-HFO-1336mzz, is removed from the top of column 101. The bottoms stream withdrawn from the bottom of 101 via stream 109 contains most of the cis and trans-HCFC-1326mxz and only a small fraction of the cis-HFO-1336mzz fed to 101 via 100. Table 8 shows the compositions of the streams entering and leaving column 101. The concentration of cis-HFO-1336mzz in stream 105 is far in excess of the cis-HFO-1336mzz concentration in the azeotrope formed by cis-HFO-1336mzz and trans-HCFC-1326mxz and the concentration of cis-HFO-1336mzz on a PCE-free basis in stream 109 is far below its azeotropic concentration. The concentration of cis-HCFC-1326mxz in stream 105 is far below its concentration in feed stream 100, indicating that the azeotrope-like behavior between cis-HFO-1336mzz and cis-HCFC-1326mxz has been overcome. This demonstrates that PCE has enabled azeotrope-forming and azeotrope-like mixtures of cis-HFO-1336mzz, cis-HCFC-1326mxz and trans-HCFC-1326mxz to be effectively separated.

TABLE 8

|  | 100 | 102 | 105 | 109 |
|---|---|---|---|---|
| Mole Fractions |  |  |  |  |
| cis-HFO-1336mzz | 0.5475 | 0 | 0.9976 | 250 ppm |
| cis-HCFC-1326mxz | 0.2262 | 0 | <<1 ppm | 0.0216 |
| trans-HCFC-1326mxz | 0.2262 | 0 | 0.0023 | 0.0215 |
| PCE | 0 | 1.0000 | 56 ppm | 0.9566 |
| Mass Fractions |  |  |  |  |
| cis-HFO-1336mzz | 0.5000 | 0 | 0.9972 | 250 ppm |
| cis-HCFC-1326mxz | 0.2500 | 0 | <<1 ppm | 0.0257 |
| trans-HCFC-1326mxz | 0.2500 | 0 | 0.0028 | 0.0255 |
| PCE | 0 | 1.0000 | 56 ppm | 0.9485 |
| Total Flow |  |  |  |  |
| lb-mole/hr | 0.5567 | 5.5666 | 0.3040 | 5.8192 |
| lb/hr | 100.0000 | 923.1639 | 49.9000 | 973.2639 |
| Temperature (° C.) | 25.0 | 50.0 | 41.5 | 103.2 |
| Pressure (psia) | 24.7 | 24.7 | 19.6 | 20.1 |

Example 13

A room temperature mixture of 80 wt % cis-HFO-1336mzz, 10 wt % trans-HCFC-1326mxz, 5 wt % cis-HCFC-1326mxz and 5 wt % CFC-1317mx is fed via stream 100 to the 20th theoretical stage from the bottom of distillation column 101 of FIG. 1. The extractive agent feed stream, comprising essentially of perchloroethylene (PCE), is fed via stream 102 to the tenth theoretical stage from the top of column 101. The molar flow rate of stream 102 is set to forty times the molar flow rate of stream 100. Distillation column 101 contains 60 theoretical stages and operates with a top pressure of approximately 5 psig and with a mass reflux flow rate (stream 104) that is twice the flow rate of stream 100. Distillate stream 105, consisting predominantly of cis-HFO-1336mzz, is removed from the top of column 101. The bottoms stream withdrawn from the bottom of 101 via stream 109 contains a majority of the CFC-1317mx, most of the cis and trans-HCFC-1326mxz, and only a small fraction of the cis-HFO-1336mzz fed to 101 via 100. Table 9 shows the compositions of the streams entering and leaving column 101.

TABLE 9

|  | 100 | 102 | 105 | 109 |
|---|---|---|---|---|
| Mole fractions |  |  |  |  |
| cis-HFO-1336mzz | 0.8317 | 0 | 0.9857 | 390 ppm |
| CFC-1317mx | 0.0394 | 0 | 0.0142 | 690 ppm |
| cis-HCFC-1326mxz | 0.0430 | 0 | <<1 ppm | 0.0011 |
| trans-HCFC-1326mxz | 0.0859 | 0 | 2 ppm | 0.0021 |
| PCE | 0 | 1.000 | 140 ppm | 0.9957 |
| Mass Fractions |  |  |  |  |
| cis-HFO-1336mzz | 0.8000 | 0 | 0.9812 | 380 ppm |
| CFC-1317mx | 0.0500 | 0 | 0.0186 | 900 ppm |
| cis-HCFC-1326mxz | 0.0500 | 0 | <<1 ppm | 0.0013 |
| trans-HCFC-1326mxz | 0.1000 | 0 | 2 ppm | 0.0026 |
| PCE | 0 | 1.000 | 145 ppm | 0.9949 |
| Total Flow |  |  |  |  |
| Lb-mole/hr | 0.5863 | 23.4520 | 0.4854 | 23.5528 |
| Lb/hr | 100.0 | 3889.2744 | 80.0 | 3909.2744 |
| Temperature (° C.) | 25.0 | 50.0 | 41.3 | 128.4 |
| Pressure (psia) 0.0430 | 24.7 | 24.7 | 19.6 | 20.1 |

Example 14

A room temperature mixture 50/50 wt % mixture of cis-HFO-1336mzz and trans-HCFC-1326mxz is fed via stream 100 to the 30th theoretical stage from the bottom of distillation column 101 of FIG. 2. The extractive agent feed stream, comprising essentially of N,N-dimethylformamide (DMF), is fed via stream 102 to the tenth theoretical stage from the top of column 101. The molar flow rate of stream 102 is set to ten times the molar flow rate of stream 100. Distillation column 101 contains 50 theoretical stages and operates with a top pressure of approximately 5 psig and with a mass reflux flow rate (stream 104) that is equal to the flow rate of 100. Distillate stream 105, consisting predominantly of trans-HCFC-1326mxz, is removed from the top of column 101. The stream withdrawn from the bottom of 101 via 109 contains almost all of the cis-HFO-1336mzz fed to 101 via 100 and all of the DMF fed to 101 via 102. Stream 109 is fed to the 7th theoretical stage from the top of a second distillation column 111 which contains 20 theoretical stages. Column 111 operates with a top pressure of approximately 5 psig and with a mass reflux flowrate (stream 114) equal to the flowrate of 109. Essentially all of the cis-HFO-1336mzz from 109 is recovered at high purity as distillate 115 from the top of 111. Essentially all of the DMF in 109 is removed as bottom stream 119 from column 111. Stream 119 is cooled and pumped by 120 and recycled to the first column as stream 102. Table 10 shows the compositions of the streams entering and leaving columns 101 and 111.

TABLE 10

|  | 100 | 102 | 105 | 109 | 115 | 119 |
|---|---|---|---|---|---|---|
| Mole Fractions | | | | | | |
| cis-HFO-1336mzz | 0.5475 | <<1 ppm | 70 ppm | 0.0519 | 1.0000 | <<1 ppm |
| trans-HCFC-1326mxz | 0.4525 | <<1 ppm | 0.9999 | 3 ppm | 50 ppm | <<1 ppm |
| DMF | 0 | 1.0000 | <<1 ppm | 0.9481 | <<1 ppm | 1.0000 |
| Mass Fractions | | | | | | |
| cis-HFO-1336mzz | 0.5000 | <<1 ppm | 60 ppm | 0.1094 | 0.9999 | <<1 ppm |
| trans-HCFC-1326mxz | 0.5000 | <<1 ppm | 0.9999 | 7 ppm | 60 ppm | <<1 ppm |
| DMF | 0 | 1.0000 | <<1 ppm | 0.8906 | <<1 ppm | 1.0000 |
| Total Flow | | | | | | |
| lb-mole/hr | 0.5567 | 5.5666 | 0.2519 | 5.8714 | 0.3048 | 5.5666 |
| lb/hr | 100.0000 | 406.8957 | 50.0000 | 456.8957 | 50.0000 | 406.8957 |
| Temperature (° C.) | 25.0 | 45.0 | 43.5 | 136.5 | 41.6 | 164.1 |
| Pressure (psia) | 24.7 | 44.7 | 19.6 | 20.1 | 19.6 | 19.8 |

Example 15

The nonpolar compounds in Table 1 will increase the volatility of cis-HFO-1336mzz relative to HCFC-1326mxz. Consequently, referring to the process shown by FIG. 2, a sufficient amount of a nonpolar extractant is fed to column 101 via line 102 so that the cis-HFO-1336mzz fed to 101 via line 100 can be preferentially distilled overhead and recovered as distillate 105. The concentration of HCFC-1326mxz in distillate 105 is less than their concentration in feed 100. At the same time, the HCFC-1326mxz fed to column 101 via line 100 is preferentially removed from the bottom of 101 via line 109 along with the extractant fed to 101 via line 102. The concentration of cis-HFO-1336mzz in bottoms stream 109 is less than its concentration in feed 100. The amount of HCFC-1326mxz present in distillate 105 and the amount of cis-HFO-1336mzz present in bottom stream 109 depend on a number of factors including: (1) the effectiveness of the particular chosen extractant, (2) the amount of extractant fed to column 101, (3) the relative amounts of cis-HFO-1336mzz, cis-HCFC-1326mxz, and trans-HCFC-1326mxz in feed 100, (4) the number of theoretical stages in column 101, (5) the locations of feeds 100 and 102 in column 101, and (6) the operating conditions (such as pressure and reflux flowrate) used for column 101.

Stream 109 is optionally heated or cooled and/or pumped by 110 and then fed to a second distillation column 111. Column 111 is designed and operated so that essentially all of the chlorofluoroolefins and cis-HFO-1336mzz in stream 109 is recovered and removed via line 115 as a second distillate and essentially all of the extractant present in 109 is recovered as a second bottoms stream 119 and recycled to the first column 101. The chlorofluoroolefin concentration in 115 is higher than in 100.

Example 16

The polar compounds in Table 2 will increase the volatility of chlorofluoroolefins relative to cis-HFO-1336mzz. Consequently, referring to the process shown by FIG. 2, when a sufficient amount of a polar extractant is fed to column 101 via line 102, the chlorofluoroolefins fed to 101 via line 100 are preferentially distilled overhead and recovered as distillate 105. The concentration of cis-HFO-1336mzz in distillate 105 is less than its concentration in feed 100. At the same time, the cis-HFO-1336mzz fed to column 101 via line 100 is preferentially removed from the bottom of 101 via line 109 along with the extractant fed to 101 via line 102. The concentration of the chlorofluoroolefins in bottom stream 109 are less than their concentration in feed 100. The amount of cis-HFO-1336mzz present in distillate 105 and the amount of chlorofluoroolefins present in bottom stream 109 depend on a number of factors including: (1) the effectiveness of the chosen extractant, (2) the amount of extractant fed to column 101, (3) the relative amounts of cis-HFO-1336mzz, and chlorofluoroolefins in feed 100, (4) the number of theoretical stages in column 101, (5) the locations of feeds 100 and 102 in column 101, and (6) the operating conditions (such as pressure and reflux flowrate) of column 101.

Stream 109 is optionally heated or cooled and/or pumped by 110 and then fed to a second distillation column 111. Column 111 is designed and operated so that essentially all of the chlorofluoroolefins and cis-HFO-1336mzz in stream 109 are recovered and removed via line 115 as a second distillate and essentially all of the extractant present in 109 is recovered as a second bottom stream 119 and recycled to the first column 101. The cis-HFO-1336mzz concentration in 115 will be higher than in 100.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for separating cis-1,1,1,4,4,4-hexafluoro-2-butene from a first mixture comprising cis-1,1,1,4,4,4-hexafluoro-2-butene and at least one chlorofluoroolefin, comprising the steps of:
   a) contacting said first mixture with at least one extractive agent, to form a second mixture;
   b) distilling said second mixture; and
   c) recovering cis-1,1,1,4,4,4-hexafluoro-2-butene substantially free of said at least one chlorofluoroolefin, wherein said at least one chlorofluoroolefin is one or more of trans-1,1,1,4,4,4-hexafluoro-2-chloro-2-butene, cis-1,1,1,4,4,4-hexafluouro-2-chloro-2-butene and 1,1,1,2,4,4,4-heptafluoro-3-chloro-2-butene.

2. The process of claim 1, wherein said at least one chlorofluoroolefin is one or more of trans-1,1,1,4,4,4-hexafluoro-2-chloro-2-butene and cis-1,1,1,4,4,4-hexafluouro-2-chloro-2-butene.

3. The process of claim 1, wherein said at least one extractive agent is a compound having a normal boiling point between 50° C. and 250° C.

4. The process of claim 1, wherein said at least one extractive agent is a C6 to C14 linear or branched alkane, C6 to C10 cyclic alkane with or without branching, C6 to C12 linear or branched alkene, C6 to 010 cycloalkene, C6 to C10 diene, C1 to C4 chloroalkane, C2 to C4 chloroalkene, or mixtures thereof.

5. The claim of claim 4, wherein said extractive agent is n-octane or perchloroethylene or mixtures thereof.

6. The process of claim 1, wherein said at least one extractive agent is an alcohol, diol, ketone, lactone, ester, anhydride, aldehyde, ether, nitrile, amide, sulfoxide, pyrrolidone, carbonate, phosphate, diethyl sulfite, dimethyl sulfate, diethyl sulfate, or mixtures thereof.

7. The process of claim 6, wherein said at least one extractive agent is ethyl acetate, n-butanol, 2-butanone, tetrahydrofuran, N,N-dimethylformamide, or mixtures thereof.

8. The process of claim 1, wherein the volatility of said cis-1,1,1,4,4,4-hexafluoro-2-butene, or said at least one chlorofluoroolefin is increased, one relative to the other, in the presence of said at least one extractive agent.

9. The process of claim 8, wherein the volatility of said cis-1,1,1,4,4,4-hexafluoro-2-butene as compared to said at least one chlorofluoroolefin is increased in the presence of said at least one extractive agent.

10. The process of claim 9, wherein said cis-1,1,1,4,4,4-hexafluoro-2-butene is recovered as an overhead stream in the said distillation.

11. The process of claim 9, wherein the extractive agent is n-octane, perchloroethylene, or mixtures thereof.

12. The process of claim 8, wherein the volatility of said cis-1,1,1,4,4,4-hexafluoro-2-butene as compared to said at least one chlorofluoroolefin is decreased in the presence of said at least one extractive agent.

13. The process of claim 12, wherein the extractive agent is ethyl acetate, n-butanol, 2-butanone, tetrahydrofuran, N,N-dimethylformamide, or mixtures thereof.

14. The process of claim 12, wherein a mixture comprising said cis-1,1,1,4,4,4-hexafluoro-2-butene and the extractive agent is recovered as bottoms stream from said distillation.

15. The process of claim 1, wherein the cis-1,1,1,4,4,4-hexafluoro-2-butene recovered from the second mixture contains less than about 1000 ppm of chlorofluoroolefin.

16. A process for reducing the concentration of an impurity, comprising:
   a. distilling a first mixture comprising cis-1,1,1,4,4,4-hexafluoro-2-butene and an impurity of at least one chlorofluoroolefin in the presence of an extractive agent which is a C6 to C14 linear or branched alkane, C6 to C10 cyclic alkane with or without branching, C6 to C12 linear or branched alkene, C6 to C10 cycloalkene, C6 to C10 diene, C1 to C4 chloroalkane, C2 to C4 chloroalkene, or mixtures thereof,
   b. recovering cis-1,1,1,4,4,4-hexafluoro-2-butene substantially free of said chlorofluoroolefin as an overhead stream from said distillation column; wherein said chlorofluoroolefin is one or more of trans-1,1,1,4,4,4-hexafluoro-2-chloro-2-butene, cis-1,1,1,4,4,4-hexafluouro-2-chloro-2-butene and 1,1,1,2,4,4,4-heptafluoro-3-chloro-2-butene.

17. The process of claim 16, wherein said chlorofluoroolefin is one or more of trans-1,1,1,4,4,4-hexafluoro-2-chloro-2-butene and cis-1,1,1,4,4,4-hexafluouro-2-chloro-2-butene.

18. The process of claim 16, wherein a bottoms stream comprising said at least one chlorofluoroolefin and extractive agent is recovered from said distillation, and subjected to a second distillation to recover said chlorofluoroolefin as an overhead stream, and the extractive agent is recovered as a bottoms stream.

19. The process of claim 16, wherein the cis-1,1,1,4,4,4-hexafluoro-2-butene contains less than about 1000 ppm of chlorofluoroolefin.

20. A process for reducing the concentration of an impurity, comprising,
   a. distilling a first mixture comprising cis-1,1,1,4,4,4-hexafluoro-2-butene and an impurity of at least one chlorofluoroolefin in the presence of an extractive agent which is an alcohol, diol, ketone, lactone, ester, anhydride, aldehyde, ether, nitrile, amide, sulfoxide, pyrrolidone, carbonate, phosphate, diethyl sulfite, dimethyl sulfate, or diethyl sulfate or mixtures thereof,
   b. removing a second mixture comprising cis-1,1,1,4,4,4-hexafluoro-2-butene and said extractive agent substantially free of said at least one chlorofluoroolefin as a bottoms composition from said distillation column,
   c. distilling said second mixture in a second distillation column, and
   d. recovering an overhead composition comprising cis-1,1,1,4,4,4-hexafluoro-2-butene substantially free of said extractive agent from the top of said second distillation column;
   wherein said at least one chlorofluoroolefin is one or more of trans-1,1,1,4,4,4-hexafluoro-2-chloro-2-butene, cis-1,1,1,4,4,4-hexafluoro-2-chloro-2-butene and 1,1,1,2,4,4,4-heptafluoro-3-chloro-2-butene.

21. The process of claim 20, wherein said at least one chlorofluoroolefin is one or more of trans-1,1,1,4,4,4-hexafluoro-2-chloro-2-butene and cis-1,1,1,4,4,4-hexafluoro-2-chloro-2-butene.

22. The process of claim 20, wherein the cis-1,1,1,4,4,4-hexafluoro-2-butene recovered from the second distillation column contains less than 1000 ppm of said chlorofluoroolefin.

* * * * *